United States Patent
Hefner, Jr. et al.

(10) Patent No.: US 12,091,377 B2
(45) Date of Patent: Sep. 17, 2024

(54) METHOD FOR CONVERTING MONOISOCYANATES TO UREAS

(71) Applicants: Dow Global Technologies LLC, Midland, MI (US); Dow Portugal Produtos Quimicos, Sociedade Unipessoal, LDA, Estarreja (PT)

(72) Inventors: Robert E. Hefner, Jr., Rosharon, TX (US); Helge Braun, Lake Jackson, TX (US); Armenio Costa, Estarreja (PT); Brian Cramm, Lake Jackson, TX (US)

(73) Assignees: Dow Global Technologies LLC., Midland, MI (US); Dow Portugal Produtos Quimicos Sociedade Unipessoal, LDA, Estarreja (PT)

( * ) Notice: Subject to any disclaimer, the term of this patent is extended or adjusted under 35 U.S.C. 154(b) by 588 days.

(21) Appl. No.: 17/295,120

(22) PCT Filed: Oct. 31, 2019

(86) PCT No.: PCT/US2019/059191
§ 371 (c)(1),
(2) Date: May 19, 2021

(87) PCT Pub. No.: WO2020/117408
PCT Pub. Date: Jun. 11, 2020

(65) Prior Publication Data
US 2022/0002237 A1 Jan. 6, 2022

Related U.S. Application Data

(60) Provisional application No. 62/776,917, filed on Dec. 7, 2018.

(51) Int. Cl.
*C07C 273/18* (2006.01)
*B01J 31/22* (2006.01)

(52) U.S. Cl.
CPC ..... *C07C 273/1818* (2013.01); *B01J 31/2234* (2013.01); *B01J 31/2295* (2013.01); *C07C 273/1809* (2013.01); *C07C 273/1872* (2013.01); *B01J 2531/22* (2013.01); *B01J 2531/845* (2013.01)

(58) Field of Classification Search
None
See application file for complete search history.

(56) References Cited

U.S. PATENT DOCUMENTS

| | | |
|---|---|---|
| 4,405,527 A | 9/1983 | Wegener |
| 4,745,216 A | 5/1988 | Keggenhoff |
| 4,820,871 A | 4/1989 | Kissener |

FOREIGN PATENT DOCUMENTS

EP 1773755 A 10/2012

OTHER PUBLICATIONS

Abramovitch et al., Tetrahedron Letters vol. 11 pp. 1065-1068 (1971).

*Primary Examiner* — Amy C Bonaparte

(57) ABSTRACT

Organic isocyanates are converted to ureas by heating in the presence of certain cobalt, magnesium, chromium and lanthanide series organometallic catalysts. The process requires no water or other reactants. The process is particularly useful for removing small quantities of monoisocyanates from a solvent stream recovered from a polyisocyanate manufacturing process. The urea compounds in some instances can be recycled back into the polyisocyanate manufacturing process and reacted with polyisocyanate compounds to form biurets.

14 Claims, No Drawings

METHOD FOR CONVERTING MONOISOCYANATES TO UREAS

This invention relates to methods for converting monoisocyanates into urea compounds.

Polyisocyanates are produced industrially in large volumes. Their primary use is as a raw material for making polyurethane and polyurea polymers.

Monoisocyanates sometimes are produced as a by-product of the manufacturing process. For example, a small amount of phenyl isocyanate is commonly produced when diphenylmethane diisocyanate (MDI) or polymeric MDI is manufactured. "Polymeric MDI" is a mixture of one or more isomers of MDI and one or more polymethylene polyphenylisocyanates that have at least three phenyl isocyanate groups.

These monoisocyanates are usually removed from the product. In the case of MDI or polymeric MDI, phenyl isocyanate is often removed when the product is separated from the reaction solvent. This produces a stream that contains solvent, most of the phenyl isocyanate and a small quantity of MDI and/or polymeric MDI.

The solvent is generally recycled, but to do so the monoisocyanate must be removed from it so the monoisocyanate does not accumulate over time. In the case of phenyl isocyanate in particular, potential toxicological concerns require that it be destroyed or converted to an innocuous product.

Some previous approaches have capitalized on the reactivity of isocyanate groups to convert the monoisocyanate to a solid material that is easily separated from the solvent. Thus, EP 1,773,755 describes catalyzing the trimerization of phenyl isocyanate to form tris(phenyl)isocyanurate. U.S. Pat. No. 4,745,216 describes reacting the phenyl isocyanate with polymer beads that have amino or hydroxyl functionality. U.S. Pat. No. 4,405,527 describes reacting the phenyl isocyanate with stoichiometric or greater amounts of polyamine or glycols to convert it to urethanes or ureas.

All of these approaches have significant shortcomings. There is the cost of added raw materials. These added raw materials represent another source of impurities which themselves must be rigorously removed from the solvent before it is recycled, again to avoid accumulation. Water is inexpensive but tends to lead to a slow reaction with low conversions of the monoisocyanates to ureas and also tends to produce monoamine by-products, which are another source of contamination. Adding stoichiometric or greater amounts of polyamines as in U.S. Pat. No. 4,405,527 can be especially problematic because they often are not entirely consumed or removed. When these polyamines are recycled with the solvent, they engage in unwanted reactions that in some cases consume the desired polyisocyanate products, decreasing yield and forming higher molecular weight impurities that increase viscosity and modify other characteristics of the product. If left in the product, the polyamines present a difficult separation problem if they are to be removed. The unreacted polyamines also can become phosgenated to form unwanted polyisocyanate species that are very difficult to remove from the desired product.

Abramovitch, in *Tetrahedron Letters* No. 11, pp. 1065-1068 (1972), describes the thermal conversion of phenyl isocyanate to a mixture of aniline and 1,3-diphenylurea in dimethylsulphoxide (DMSO) solution. The same reference reports that no such reaction takes place when the DMSO is replaced with a non-polar hydrocarbon solvent, including benzene. The use of DMSO as a solvent is impractical on an industrial scale. The phosgenation solvent is typically a non-polar hydrocarbon or halogenated hydrocarbon. Converting phenyl isocyanate to the symmetrical urea in DMSO would require a solvent transfer process, which would be prohibitively expensive at large scale.

This invention is a method for converting an organic isocyanate comprising a phenyl isocyanate to one or more urea compounds in the presence of a non-polar organic solvent. The method comprises reacting a solution of the organic isocyanate in a liquid nonpolar solvent in the presence of at least 0.025 wt.-% of an organometallic catalyst, based on the weight of the organic isocyanate, wherein the organometallic catalyst is selected from the group consisting of bis(cyclopentadienyl) Cr(II), bis(methylcyclopentadienyl Cr(II) and compounds having at least one metal ion bonded to at least one organic ligand wherein the metal ion is selected from one or more of Co(II), Mg(II), Y(III), Cr(III) and a lanthanide series metal ion in the 3+ oxidation state, to convert at least a portion of the organic isocyanate to the one or more urea compounds.

The organometallic catalysts are surprisingly effective in promoting the reaction of the organic isocyanate. It is believed that at least one isocyanate group of the organic isocyanate reacts in the presence of the catalyst to form the corresponding amino group. This amino group can react with an isocyanate group of another molecule of the organic isocyanate to form a urea. Importantly, the reaction takes place at good rates even when the solvent is a non-polar type such as is typically used in industrial scale isocyanate production processes. This represents a very significant economic advantage of the invention.

In many cases, the urea compound(s) thus formed remain at least partially soluble in the liquid nonpolar solvent, which can reduce or eliminate the need to perform a solid/liquid separation step.

It has further been found that the urea compounds and aniline (if any) formed in the foregoing process can be recycled, each in small quantities, back into a polyisocyanate production process. The urea compound(s) can react with the polyisocyanate under the conditions of distillation process commonly used to separate the polyisocyanate from the process solvent, forming a small quantity of biuret-containing species. When the amount of recycled urea is small, these biuret-compounds have minimal effects on product properties such as isocyanate equivalent weight and functionality. Accordingly, the product containing those species can substitute directly for the unmodified polyisocyanate in most if not all applications. Any residual aniline that has not reacted to form a urea compound may likewise react with the polyisocyanate under the conditions of distillation process commonly used to separate the polyisocyanate from the process solvent, forming a small quantity of urea-containing species. Because the amount of phenyl isocyanate by-products produced in an industrial-scale polyisocyanate facility is usually quite small, this invention provides a route via which most if not all of the phenyl isocyanate by-products can be recycled, thereby greatly reducing if not eliminating the need to dispose of the phenyl isocyanate and/or ureas and/or aniline formed therefrom.

Therefore, some embodiments of the invention further comprise a step of reacting the urea compounds with an excess of a polyisocyanate to produce a biuret- and urea-modified polyisocyanate composition.

In particular embodiments, the invention is an MDI and/or polymeric MDI manufacturing process, comprising the steps of:

a) reacting aniline with formaldehyde to produce a mixture of methylene dianiline (MDA), one or more polymethylene polyanilines having at least three aniline groups (PMDA), and unreacted aniline in the solvent;

b) distilling aniline from the mixture produced in step a) to produce a process stream containing the MDA, PMDA and residual aniline;

c) phosgenating the process stream from step b) in a non-polar solvent to form an isocyanate process stream containing the non-polar solvent, MDI, one or more polymethylene polyphenylisocyanates that have at least three phenyl isocyanate groups (PMDI) and phenyl isocyanate;

d) separating MDI and PMDI from the isocyanate process stream obtained in step c) by distillation to produce a solvent stream containing the non-polar solvent, 0.2 to 10 weight percent phenyl isocyanate based on the weight of the solvent stream and up to 5 weight percent, based on the weight of the solvent stream, of MDI and/or PMDI;

e) reacting the solvent stream obtained in step d) in the presence of at least 0.025 wt.-% of an organometallic catalyst, based on the weight of the phenyl isocyanate, wherein the organometallic catalyst is selected from the group consisting of bis(cyclopentadienyl) Cr(II), bis (methylcyclopentadienyl Cr(II) and compounds having at least one metal ion bonded to at least one organic ligand wherein the metal ion is selected from one or more of Co(II), Mg(II), Y(III), Cr(III) and a lanthanide series metal ion in the 3+ oxidation state, to convert at least a portion of the phenyl isocyanate to 1,3-diphenylurea and optionally aniline, and optionally to thermally deactivate the organometallic catalyst; and f) recycling 1,3-diphenylurea, aniline, and optionally non-polar solvent and optionally residues from the thermal deactivation of the catalyst from step e) directly or indirectly into step d), whereby at least a portion of the 1,3-diphenylurea reacts with at least a portion of the MDI and/or PMDI to form one or more biuret compounds and at least a portion of the aniline, if any, reacts with least a portion of the MDI and/or PMDI to form one or more urea compounds.

The starting organic isocyanate includes a phenyl isocyanate, which for purposes of this invention is a compound having only one isocyanate group, which isocyanate group is directly bonded to a ring carbon of an aromatic ring (preferably a benzene ring). The phenyl isocyanate may be unsubstituted, i.e., is phenyl isocyanate having the structure:

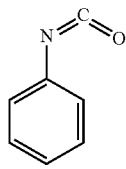

and/or may be substituted on any one or more of the ring carbons. Among the substituted phenyl isocyanates are monochloro isomers of phenyl isocyanate including 2-chlorophenyl isocyanate, 3-chlorophenyl isocyanate, and 4-chlorophenyl isocyanate; dichlorophenyl isocyanates including 2,4-dichlorophenyl isocyanate, 2,6-dichlorophenyl isocyanate, 3,4-dichlorophenyl isocyanate and 3,5-dichlorophenyl isocyanate; as well as chloroalkyl-substituted phenyl isocyanates such as p-chloromethylphenyl isocyanate and o-chloromethylphenyl isocyanate. Mixtures of any two or more of the foregoing (including mixtures of phenyl isocyanate and any one or more substituted phenyl isocyanates as described above) may be used.

The organic isocyanates may include other isocyanate compounds, including one or more polyisocyanate compounds. Of particular interest are MDI (diphenylmethane diisocyanate), which may be any one or more of the 2,2'-, 2,4'- or 4,4'-isomers, and one or more polymethylene polyphenylisocyanates that have at least three phenyl isocyanate groups, as well as polymeric MDI. Also useful are any of the foregoing that are modified to include urea, urethane, carbodiimide, uretdione, allophanate and/or biuret groups.

A mixture of a phenyl isocyanate and one or more other organic isocyanates can be used as the starting organic isocyanate. In such mixtures, it is preferred that the other organic isocyanate(s), if present at all, be present in relatively small quantities compared to the monoisocyanate. The other organic isocyanate(s), if present at all, may constitute at least 0.0001%, at least 0.1%, at least 0.2%, at least 0.5%, at least 1% or at least 1.5% of the weight of the starting isocyanate solution, and may constitute up to 5%, up to 4%, or up to 3% thereof.

The organic isocyanate(s) are dissolved in one or more nonpolar organic solvents. The solvent is further generally characterized as having a boiling temperature (at one standard atmosphere pressure) of at least 60° C. and being (i) a solvent for the organic isocyanate, (ii) devoid of isocyanate groups and (iii) inert, i.e., non-reactive toward isocyanate groups and reaction products (including intermediates such as amines) which form under the conditions of the process. Examples of suitable solvents include halogenated aromatic compounds such as monochlorobenzene, o-dichlorobenzene, p-dichlorobenzene and m-dichlorobenzene, various trichlorobenzene isomers, mixtures thereof, and the like. Other suitable solvents include, for example, benzene, toluene, para-xylene, and various aliphatic hydrocarbons that can be halogenated or non-halogenated, mixtures of any two or more thereof, and the like.

The organic isocyanate(s) preferably are present as a somewhat dilute solution in the solvent(s). The organic solvent(s) may constitute, for example, at least 90% of the combined weight of the solvent(s) and organic isocyanate(s). In particular embodiments, the organic solvent(s) may constitute at least 95% of the weight thereof, and may constitute up to 99.8%, up to 99.5%, up to 99% or up to 98.5% thereof.

The phenyl isocyanate(s) may constitute, for example, up to 10%, up to 5%, up to 4% or up to 3% of the weight of the starting solution. In particular embodiments the phenyl isocyanate(s) constitute at least 0.2%, at least 0.5%, at least 1% or at least 1.5% of the weight of the starting solution.

The starting solution may be or include a process stream from a polyisocyanate manufacturing facility. Polyisocyanates are sometimes manufactured by reacting a polyamine with phosgene in solution. Upon separation of the solvent from the polyisocyanate product, a process stream is sometimes produced that contains, in addition to the solvent, small quantities of monoisocyanate(s) and in some cases small quantities of polyisocyanates. Such a process stream is a useful starting solution for the process of this invention.

In a particular embodiment, the process stream is taken from a diphenylmethane diisocyanate (MDI) production facility. MDI and polymeric MDI are made industrially by condensing aniline with formaldehyde to ultimately produce methylene dianiline (MDA) and/or polymethylene polyanilines that have 3 or more aniline groups (PMDA), which are then reacted with phosgene in solution to produce the corresponding polyisocyanates. A small amount of unreacted aniline becomes phosgenated to produce phenyl isocyanate. When the product is separated from the reaction solvent, a process stream is produced that contains the solvent, a small quantity of phenyl isocyanate and often a small quantity of MDI and/or PMDI. This process stream is a useful starting solution for the process of this invention.

The catalyst is an organometallic catalyst selected from the group consisting of bis(cyclopentadienyl) Cr(II), bis (methylcyclopentadienyl Cr(II) and compounds having at least one metal ion selected from one or more of Co(II), Mg(II), Y(III), Cr(III) and a lanthanide series (La, Ce, Pr, Nd, Sm, Eu, Gd, Tb, Dy, Ho, Er, Tm, Yb or Lu) metal ion in the 3+ oxidation state. Co(II) and Mg(II) are especially preferred.

The metal ion is bonded (covalently, including by haptic covalent bonds, anionically or otherwise) to at least one organic ligand and may, in addition, be bonded to one or more inorganic ligands and/or anions to balance the charges and form an electrostatically neutral compound or complex.

Examples of organic ligands include, for example, arene ligands, which may have at least one ring of 4 or more, especially 5, 6, 7 or 8, members. The ring may contain one or more heteroatoms such as, for example, boron or nitrogen. Such arene ligands may be, for example, phenyl, substituted phenyl, cyclopentadienyl and substituted cyclopentadienyl such as methylpentadienyl, dicarbollide, cyclooctatetraene, fullerene and the like. An arene ligand may be bonded to a polymer structure if desired, and this may be done to provide a heterogeneous catalyst. The ligand preferably does not include nitrogen atoms.

In some embodiments, the metallic catalyst is a "sandwich" or "half-sandwich" compound in which the metal ion is bonded to two or one, respectively, such arene groups. In the former case, the metal ion is positioned between the arene groups. In either case, the metal ion may be in addition bonded to one or more other ligands or anions such as carbonyl, hydrocarbon, halide, hydroxide, nitro or the like, and two metal ions may be present in the structure.

In particular embodiments, the metal catalyst is a metallocene in which the metal ion is bonded to two or more cyclopentadiene rings (which may optionally be substituted) and optionally one or more other ligands and/or anions. Bis(cyclopentadienyl) metal compounds are particularly preferred.

In other embodiments, one or more of the ligands is a β-diketone, i.e., one including at least one

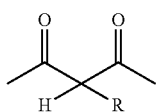

moiety, where R is hydrogen or an organic group (preferably hydrogen), or the corresponding tautomeric enol. Examples of such β-diketone ligands include acetylacetonate, ethyl acetonate, pyrollidine-2,4-dione and

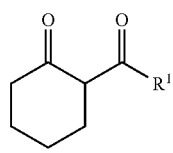

wherein $R^1$ is hydrocarbyl or substituted hydrocarbyl and the cyclohexane ring may be substituted at one or more of the carbon atoms. The R and $R^1$ groups independently may contain, for example, up to 24, up to 12, up to 8, up to 6, up to 4 or up to 2 carbon atoms.

Specific metal catalysts include bis(cyclopentadienyl)Co (II), bis(cyclopentadienyl) Mg (II), bis(cyclopentadienyl Cr(II), tris(cyclopentadienyl) Cr (III), tris(cyclopentadienyl) Gd (III), tris(cyclopentadienyl) Y (III), tris(cyclopentadienyl) La (III), bis(methylcyclopentadienyl) Co (II), bis(methylcyclopentadienyl) Mg (II), bis(methylcyclopentadienyl Cr(II), tris(methylcyclopentadienyl) Gd (III), tris(methylcyclopentadienyl) Y (III), tris (methylcyclopentadienyl) La (III), Co (II) acetylacetonate, bis(2,4-pentanedionato) Mg (II), and the corresponding compounds of any one or more of the other lanthanide series metals (Ce, Pr, Nd, Sm, Eu, Tb, Dy, Ho, Er, Tm, Yb or Lu).

The amount of catalyst is at least 0.025 wt.-%, based on the weight of the isocyanate(s). A preferred amount is at least 0.035 wt.-%. Any greater amount can be used, but adequate results are obtained when the amount of catalyst is 2 wt.-% or less, 1 wt.-% or less or even 0.5 wt.-% or less.

The catalyst may be supported on an inorganic or organic support if desired. The catalyst may be supported on or bound to a polymeric backbone. In such cases, the weight of the support or polymeric backbone is ignored in calculating the weight of catalyst per unit weight of isocyanate(s).

It is also preferred that the reaction mixture is essentially devoid of water. For purposes of this invention, the reaction mixture (or any ingredient thereof individually) is considered as being essentially devoid of water if it contains no more than 0.05 wt.-% thereof, based on the total weight thereof. The reaction mixture preferably contains no more than 0.01 wt.-% of water.

The mixture of solvent, organic isocyanate and catalyst is held at a temperature of at least 0° C. for a period of at least 5 minutes to convert at least a portion of the organic isocyanate to a urea compound. The temperature preferably is such that the solvent remains at or below its boiling temperature under the pressure conditions of the reaction, and below a temperature at which the catalyst degrades and/or deactivates. The temperature preferably is at least 20° C., at least 60° C., at least 70° C. or at least 80° C. and may be up to, for example, 225° C., up to 180° C., up to 150° C., up to 130° C., up to 120° C., up to 110° C. or up to 100° C. The temperature employed will depend on the desired rate of conversion of phenyl isocyanate to 1,3-diphenylurea and the thermal stability of the specific organometallic catalyst employed in the particular solvent used.

The reaction is performed for a period of time long enough to convert at least a portion of the organic isocyanate(s) to one or more urea compounds. Some small amount of other side reactions, including biuret formation, may occur, and a small amount of aniline is typically produced but in some cases is fully consumed by reaction to urea compounds. Preferably, the reaction is performed for a period of time sufficient to consume at least one-third or at least one-half of the starting quantity of organic isocyanate (s) to urea compounds (and biuret compounds, if any). A suitable reaction time is at least 5 minutes, at least 10 minutes, at least 20 minutes or at least 30 minutes at a temperature of 60° C. or greater. Any longer period of time may be used, but in general reaction times in excess of 12 hours are unnecessary. A preferred reaction time is up to 10 hours, up to 8 hours or up to 6 hours.

The reaction pressure may range considerably from subatmospheric to superatmospheric. The pressure should be high enough such that the organic isocyanate and solvent do not volatilize at the reaction temperature. The absolute reaction pressure may be, for example, at least 0.1 atmosphere, at least 0.5 atmosphere, at least 0.9 atmosphere and, for example, up to 10 atmospheres, up to 5 atmospheres, up to 2 atmospheres or up to 1.25 atmospheres. The reaction preferably is performed under an inert atmosphere such as nitrogen, helium or argon. Likewise, thermal degradation of the organometallic catalyst is preferably conducted under an inert atmosphere, such as nitrogen.

Although the invention is not limited to any theory, it is believed that a portion of the isocyanate groups of the starting organic isocyanate compound(s) react under the reaction conditions to form the corresponding primary amine. In particular, phenyl isocyanate is converted to aniline. The primary amine group is highly reactive toward isocyanate groups, and therefore reacts with unconverted isocyanate compound(s) to form the corresponding urea compound(s). As mentioned above, some trace amount of biuret formation often is seen as the urea compound(s) react further with isocyanates. Longer reaction times and higher reaction temperatures generally favor formation of minor amounts of co-products.

In the simple case in which only phenyl isocyanate is present, the urea product is generally 1,3-diphenylurea. Substituted phenyl isocyanates tend to form the corresponding symmetrical urea products.

A more complex mixture of urea compounds forms when a polyisocyanate is present and/or a mixture of isocyanate compounds are present.

An advantage of the invention is that the organometallic catalyst often can be thermally deactivated. The thermal deactivation step is performed at a higher temperature than that of the urea-forming reaction step. Thus, in some embodiments, the urea-forming step is performed at a first, lower temperature, followed by a catalyst deactivation step, which is performed at a second, higher temperature. The first, lower temperature is below that at which the catalyst deactivates or decomposes, whereas the second, higher temperature is such that the catalyst deactivates or decomposes. The first, lower temperature may be as set forth before; the second, higher temperature may be at least 100° C., at least 120° C. or at least 130° C., but in any case is higher than the first, lower temperature at which the urea compounds are formed. It is also within the scope of the present invention, although not preferred, to add one or more compounds to induce deactivation of the organometallic catalyst. For air-sensitive organometallic catalysts, introduction of air may be useful to deactivate the catalyst.

These urea compound(s) formed may be soluble, partially soluble, or insoluble in the solvent. In cases in which a mixture of urea compounds is produced, some may be soluble or partially soluble, and others may be insoluble in the solvent. Solid ureas may be separated from the solvent by any convenient solid-liquid separation techniques such as decantation, filtration, vacuum filtration, centrifugation, flocculation or settling. The organic solvent, after separation from the urea compounds, contains a reduced amount of the starting isocyanate compound(s), if any at all, and a reduced amount of the amine compound, if any. In an industrial polyisocyanate manufacturing setting, this separated organic solvent may be recycled back into polyisocyanate manufacturing process at any point downstream of the phosgenation reaction, and/or recycled back into the process of this invention. The urea compounds separated from the organic solvent may also include residues obtained by deactivation of the organometallic catalyst.

The urea compounds separated from the organic solvent may be discarded, burned or otherwise disposed of. By converting organic isocyanates to urea compounds, toxicological and other concerns associated with the handing and disposal of the isocyanates are at least partially alleviated.

The urea compound(s) produced in the process of the invention can react with isocyanate compounds under certain conditions to form biuret compounds. Likewise, any residual unreacted amine compounds (such as aniline) can react with isocyanate compounds to form urea compounds. Therefore, in some embodiments of the invention, some or all of the urea compound(s) are combined with a polyisocyanate and caused to react with the polyisocyanate to produce a composition that contains one or more biuret compounds that correspond to the reaction product of one or more of the urea compound(s) and the polyisocyanate. Likewise, some or all of any unreacted amine compound is combined with a polyisocyanate and caused to react with the polyisocyanate to produce a composition that contains one or more urea compounds.

Suitable conditions for biuret formation include an elevated temperature, such as at least 100° C. or at least 120° C. and, for example, up to 230° C. or up to 200° C. A reaction time of 1 to 300 minutes is generally suitable, and a more preferred reaction time is 1 to 120 minutes or 5 to 60 minutes. Pressures may be superatmospheric, atmospheric or subatmospheric. The reaction may be performed in a solvent such as those described above. The aforementioned conditions are also suitable for urea formation.

Such a biuret-forming reaction is conveniently performed by recycling the nonpolar solvent containing the urea compound(s) plus any residual unreacted amine compound back into the isocyanate manufacturing process, at any point downstream of the phosgenation step. An isocyanate manufacturing process often includes a step of separating the isocyanate product from the process solvent. This separation is often performed by distillation, which distillation conditions typically include temperature and other conditions suitable for biuret and urea formation.

Accordingly, in a preferred process, the nonpolar solvent containing the urea compounds plus any residual unreacted amine compound is recycled into the isocyanate manufacturing process, and the resulting process stream containing process solvent (including the recycled solvent), isocyanate compounds, urea compounds (such as 1,3-diphenyl urea), and amine compounds (such as aniline) is subjected to a distillation step. The distillation step is performed at a temperature as described above with regard to the biuret-forming step, such that biuret formation, urea formation, and polyisocyanate product recovery from the process solvent are achieved simultaneously. This distillation step may be performed at a subatmospheric pressure if desired. This results in a substantially solvent-free polyisocyanate composition containing biuret and urea structures and a distillate stream containing solvent, which distillate stream typically will contain a small amount of monoisocyanate(s) and possibly polyisocyanates that distill with the solvent.

The weight ratio of urea compounds to isocyanate compounds should be low, such as 0.001 to 5 parts by weight of urea compounds per 100 parts by weight of isocyanate compounds. A more preferred amount is 0.005 to 2.5 parts, 0.01 to 1.5 parts or 0.01 to 1 part, on the same basis. If present, the weight ratio of amine compounds (including aniline) to isocyanate compounds should be low, such as 0.001 to 5 parts by weight of amine compounds per 100 parts by weight of isocyanate compounds. A more preferred amount is 0.005 to 2.5 parts, 0.01 to 1.5 parts or 0.01 to 1 part, on the same basis.

When the urea compounds are to be recycled in the manner just described, it is preferred that at least 90%, more preferably at least 95%, of the total weight of the starting isocyanate compound is a phenyl isocyanate. Urea compounds made from such a phenyl isocyanate tend to have low molecular weights, and form lower molecular weight biuret compounds in the subsequent biuret-forming step.

In a particular embodiment, the starting solution is or includes a process stream from a MDI and/or polymeric MDI manufacturing facility. Such a production facility includes a phosgenation unit in which phosgene is reacted with MDA and/or a mixture of MDA with one or more PMDAs to produce the polyisocyanate compounds. Such a production facility may also include an upstream unit in which aniline and formaldehyde are reacted to produce the MDA and/or PMDA. In such a production facility, the aniline is typically present in excess, and the excess is distilled from the product and recycled. Small amounts of aniline that are not removed in the distillation step are introduced into the phosgenation unit and converted to phenyl isocyanate. When the solvent is separated from the MDI and/or polymeric MDI, a process stream is formed in which all or a portion of the phenyl isocyanate is concentrated in the solvent. In these embodiments, this process stream forms all or a part of a starting solution for use in the 1,3-diphenylurea and aniline-forming process of this invention.

Such a process stream includes the organic solvent (which is preferably a chlorinated benzene compound), phenyl isocyanate and optionally but typically a small amount of 2,4'-; 4,4'- and/or 2,2'-MDI. The phenyl isocyanate content may be 0.05 to 10% by weight and is more typically 0.1 to 3% by weight, based on the weight of the process stream, and the MDI may constitute up to 1% by weight on the same basis.

In this particular embodiment, the main urea compound formed in the reaction is 1,3-diphenylurea and the main amine compound formed is aniline. In such a case, it is preferred to recycle at least the urea compound(s) and preferably the entire the product, including product formed from the deactivation of the organometallic catalyst, back into the isocyanate-manufacturing process, at any point downstream of the phosgenation step, for biuret and urea formation as described before. Biuret and urea formation preferably is performed during a flashing and/or distillation step in which the MDI and/or PMDI is separated from the process solvent.

In cases in which the urea compound(s) are separated from the nonpolar solvent, the solvent after separation from the urea compounds is conveniently recycled back into the process at any point of the isocyanate manufacturing process downstream of the phosgenation.

Ureas and amines formed in accordance with the invention, when recycled into the MDI and/or PMDI manufacturing process in small amounts as described above, produce biuret and urea-containing isocyanate products that can be used in the same manner as the unmodified MDI and/or PMDI products. Depending on the amount of ureas and amines recycled into the MDI and/or PMDI, product viscosities are increased slightly if at all. Molecular weights ($M_n$, $M_w$, $M_z$) and polydispersities (all as measured by GPC against 1000 molecular weight polyethylene glycol standards) all increase slightly, if at all. Isocyanate content and functionality decrease slightly. Generally, when less than about 1.0 part by weight of urea compounds per 100 parts by weight of isocyanate compounds are recycled, no significant change in the properties, utility or performance of the biuret and urea-containing isocyanate products is detected.

The following examples are provided to illustrate the invention, but are not intended to limit the scope thereof. All parts and percentages are by weight unless otherwise indicated.

EXAMPLES 1-4

General procedure: A standard solution of about 2 wt.-% phenyl isocyanate in chlorobenzene is prepared. A sample of the standard solution is combined with the catalyst under nitrogen in a 3 neck, 100 milliliter, round bottom, glass reactor equipped with a chilled condenser (0° C.), thermocouple/heating mantle/temperature controller assembly, overhead nitrogen inlet (0.2 LPM), and magnetic stirring. The resulting mixture is heated over 9-12 minutes to 80° C. and maintained at that temperature. The reaction is followed by taking samples periodically and analyzing them for phenyl isocyanate, aniline, and 1,3-diphenylurea, using an externally calibrated gas chromatograph.

In each of Examples 1-4, the catalyst is bis(cyclopentadienyl)cobalt (II). The amount of catalyst (as a percentage of the weight of phenyl isocyanate solution) is as reported in Table 1.

TABLE 1

| Example | Catalyst | Concentration, wt-% |
|---------|----------|---------------------|
| 1 | Bis(cyclopentadenyl) Co(II) | 0.365% |
| 2 | Bis(cyclopentadenyl) Co(II) | 0.16% |
| 3 | Bis(cyclopentadenyl) Co(II) | 0.048% |
| 4 | Bis(cyclopentadenyl) Co(II) | 0.0385% |

In each case, the amount of phenyl isocyanate is reduced by greater than 50% within a few minutes after the start of the reaction. After 5-6 hours of reaction time, the concentration of phenyl isocyanate is reduced to about 0.06% or less in each case. A similar amount of aniline is detected at that time. A strong 1,3-diphenylurea peak is detected in each case beginning at about 30-40 minutes of reaction time.

The reaction solutions from Examples 2 and 4 are each subjected to further processing to thermally deactivate the catalyst. In each case, the solution is heated to reflux (133.7-133.9° C.) over 13 minutes. Some fine brown particles are observed suspended in the solution, indicating that the catalyst has been thermally deactivated. After 3 hours heating at reflux, heating is discontinued and the reactor is allowed to cool to room temperature. Chlorobenzene is removed from each of the resulting solutions using a rotary evaporator operated to final conditions of 75° C. and 0.9-1.6 mm Hg. In each case, a brown solid is recovered, which consists mainly of 1,3-diphenylurea, and deactivated catalyst residues.

0.5 parts of solids thus obtained in each case are combined under nitrogen with 100 parts of a commercial grade polymeric MDI (PAPI™ 27, from The Dow Chemical Company) at a weight ratio. The solution is heated over 35 minutes to 100° C. and held at that temperature for 20 minutes, further heated to 125° C. over 16 minutes, and held at that temperature for 1 hour. Biuret compounds form under these conditions as confirmed by Matrix-Assisted Laser Desorption/Ionization Mass Spectral (MALDI-TOF MS) analysis. The solutions are in each case then cooled to 109° C. and vacuum filtered. The supernatant fluid is a transparent amber brown colored solution that is liquid at room temperature.

The isocyanate content of the supernatant liquid is determined by titration. For comparison, a quantity of the polymeric MDI is heated in similar manner by itself, and its isocyanate content then measured. Viscosity is measured using a cone-and-plate viscometer with a 40 mm cone and 54 μm gap at 25.6° C. and 100° C. Number and weight average molecular weights are measured by gel permeation chromatography against a 1000 mw polyethylene glycol standard. Results are as indicated in Table 2.

TABLE 2

| Designation | Isocyanate content (wt.-%) | Viscosity, Pa · s, 25.6° C./100° C. | $M_n/M_w/$ Polydipersity |
|---|---|---|---|
| Polymeric MDI | 32.65 | 0.20/0.01 | 450/574/1.276 |
| Polymeric MDI biuret-modified with Ex. 2 | 31.73 | 0.22/0.01 | 449/578/1.286 |
| Polymeric MDI biuret-modified with Ex. 4 | 31.91 | 0.25/0.01 | 452/581/1.286 |

As the data in Table 2 shows, modifying a polymeric MDI with a small (in this case, 0.5 wt-%) amount of the 1,3-diphenylurea containing residues from the deactivation of the organometallic catalyst results in at most a very small change in isocyanate content, viscosity and molecular weight. Isocyanate functionality is also essentially unchanged. The data also demonstrates that the residues from the deactivated organometallic catalyst have little, if any, effect on the properties of the polymeric MDI. This data indicates that biuret-modified polyisocyanates produced by reaction with a small quantity 1,3-diphenylurea are useful in the same manner and in the same applications as the unmodified polyisocyanates.

EXAMPLES 5-6

The general procedure is repeated, replacing the cobalt catalyst of Examples 1-4 with various quantities of bis(cyclopentadienyl)magnesium (II). The amount of catalyst and results are as indicated in Table 3:

TABLE 3

| Designation | Bis(cyclopentadienyl) Mg (II), wt.-% | Results |
|---|---|---|
| 5 | 0.36 | Phenyl isocyanate and aniline levels are each below 0.1 wt.-% after 300 minutes; large 1,3-diphenylurea peak detected. |
| 6 | 0.076 | Phenyl isocyanate concentration reduces to 1.47 wt.-% with 0.02 wt.-% aniline after 2 hours and further to 0.93 wt-% phenyl isocyanate and 0.03 wt.-% aniline after 23 hours; 1,3-diphenylurea peak detected. |

The data in Table 3 demonstrates the effect of catalyst concentration.

EXAMPLE 7

The general procedure is repeated using a concentration of 0.020 wt.-% bis(cyclopentadienyl)magnesium (II). The solution is heated over 16 minutes to reflux (133° C.) and sampled for externally calibrated gas chromatographic analysis, demonstrating a decrease in phenyl isocyanate from 1.99 to 1.80 w.-%, with no aniline detected. Some fine orange particles are observed suspended in the solution, indicating that the catalyst has been thermally deactivated. After heating at reflux for an additional 6 hours phenyl isocyanate and aniline concentrations are unchanged.

The general procedure is repeated using a concentration of 0.012 wt.-% bis(cyclopentadienyl)magnesium (II). The solution is heated over 12 minutes to 80° C. and sampled for externally calibrated gas chromatographic analysis after holding at 80° C. for 7 hours, demonstrating a decrease in phenyl isocyanate from 2.06 to 1.74 w.-%, with 0.014 w.-% aniline detected. After heating at reflux for an additional 16.35 hours phenyl isocyanate decreases to 1.44 w.-% with 0.022 w.-% aniline detected.

The results demonstrate thermal deactivation of the bis(cyclopentadienyl)magnesium (II) catalyst at 133° C., with no additional decrease in phenyl isocyanate concentration after this temperature is achieved. Even when a lower catalyst concentration (0.012 wt.-%) is employed, phenyl isocyanate concentration continues to decline at 80° C.

EXAMPLES 8-13 AND COMPARATIVE SAMPLES C-N

The general procedure is repeated, substituting other catalysts for the catalyst of Examples 1-4. Results are as indicated in Table 4.

TABLE 4

| Designation | Catalyst | Wt.-% Catalyst | Result |
|---|---|---|---|
| 8 | Bis(cyclopentadienyl) Cr(II) | 0.36 | Phenyl isocyanate concentration < 1.4 wt.-% after about 5 hours. |
| 9 | Tris(cyclopentadienyl) Gd(III) | 0.36 | Phenyl isocyanate concentration < 1.4 wt.-% after about 3 hours. |
| 10 | Co(II) acetylacetonate | 0.36 | Phenyl isocyanate concentration < 1.3 wt.-% after about 5 hours. |
| 11 | Tris(cyclopentadienyl) Y(III) | 0.36 | Phenyl isocyanate concentration < 1.5 wt.-% after about 71 minutes. |
| 12 | Bis(2,4-pentanedionato) Mg(II) | 0.36 | Phenyl isocyanate concentration < 1.4 wt. % after about 190 minutes. |
| 13 | Tris(cyclopentadienyl) La(III) | 0.36 | Phenyl isocyanate concentration < 1 wt-% within 129 minutes. |
| C* | Bis (cyclopentadienyl) Fe(II) | 0.17 | No reaction after over 5 hours. |
| D* | Bis (cyclopentadienyl) Fe(II) | 0.36 | No reaction after 6 hours. |
| E* | Methylcyclopentadienyl Mn(I) tricarbonyl | 0.36 | No reaction after 7 hours. |
| F* | Bis(cyclopentadienyl) Ru(II) | 0.36 | No reaction after 7 hours. |
| G* | Bis(cyclopentadienyl) V(II) | 0.36 | Minimal reaction after 6 hours. |
| H* | Bis*cyclopentadienyl) Mo(IV) dichloride | 0.36 | No reaction after 7 hours. |
| I* | Fe(II) acetylacetonate | 0.36 | No reaction after 7 hours. |
| J* | Co(III) acetylacetonate | 0.36 | No reaction after 7 hours. |
| K* | Cyclopentadienyl Co(I) dicarbonyl | 0.36 | No reaction after 7 hours. |
| L* | Bis(cyclopentadienyl Ni(II) | 0.36 | Minimal reaction after 400 minutes. |

TABLE 4-continued

| Desig-nation | Catalyst | Wt.-% Catalyst | Result |
|---|---|---|---|
| M* | Bis(cyclopentadienyl) dimethyl Zr(IV) | 0.36 | Minimal reaction after 435 minutes. |
| N* | Co(II) chloride | 0.36 | No reaction after 4½ hours. |
| O* | Cobalt II) phthalocyanine | 0.05 | No reaction after 2½ hours, at 80° C. or 2 hours additional at 134° C. |

The data in Table 4 shows the effect of catalyst selection. The Cr(II), Gd(III), Y(III), and La(III) cyclopentadienyl compounds all exhibit significant activity. Co(II) and Mg(II), when complexed with dione ligands, also exhibit significant activity.

Surprisingly, the Co(I) and Co(III) compounds tested do not exhibit catalyst activity in this reaction, suggesting that the oxidation state of those metals is important to their catalytic performance. Similarly, the inorganic Co(II) salt (cobalt dichloride) perform poorly, suggesting that the organic ligand is important to catalytic activity. Likewise Co (II) phthalocyanine dp not exhibit catalytic activity, apparently due to partial bonding between the Co(II) and the nitrogen atoms of the phthalocyanine.

Other organometallic catalysts tested perform poorly or not at all.

Recycling Method Model Reaction

To further simulate and evaluate the effect of recycling urea compounds and aniline obtained in the process of the invention, the following model reaction is performed.

Aniline (0.248 gram, 2.663 milliequivalents amine) in chlorobenzene (8.01 grams) is combined with a solution prepared by combining 0.05 wt-% diphenylmethane diisocyanates (MDI), 2 wt-% phenyl isocyanate, and 97.95 wt-% chlorobenzene (25.072 grams, 4.309 NCO milliequivalents). The diphenylmethane diisocyanates used are an approximate 50 wt-% 4,4'- and 50 wt-% 2,4'-isomer mixture. After holding at reflux, followed by cooling, vacuum filtration of the slurry on a fritted glass funnel, and drying at 100° C. in the vacuum oven, a white powder is recovered.

Matrix Assisted Laser Desorption Ionization Mass Spectrometry (MALDI)-Orbitrap analysis of a portion of the reaction product is completed, examining the region from 50-650 Daltons (Da). The major peak intensities are due to (DPU)H$^+$ at 213.1022 Da and (DPU)Na$^+$ at 235.0842 Da (DPU=diphenylurea). The minor peak intensities are due to (aniline)H$^+$ at 94.0651 Da, (DPU with a single biuret linkage)Na$^+$ at 354.1213 Da, (bis[urea]MDI)Na$^+$ at 459.1792 Da, and (bis[urea]MDI with a single biuret linkage)Na$^+$ at 578.2163 Da.

This data confirms the reaction products of the process of the invention form mainly compounds having a single biuret linkage or none at all. A portion of the 1,3-diphenylurea produced in the inventive process does not react further under these conditions.

What is claimed is:

1. A method for converting an organic isocyanate comprising one or more isocyanates, wherein at least one of the one or more isocyanates is a substituted or unsubstituted phenyl isocyanate, to one or more urea compounds in the presence of a non-polar organic solvent, comprising reacting a solution of the organic isocyanate in a liquid nonpolar organic solvent in the presence of at least 0.025 wt.-% of a organometallic catalyst, based on the weight of the organic isocyanate, wherein the organometallic catalyst is selected from the group consisting of bis(cyclopentadienyl) Cr(II), bis(methylcyclopentadienyl) Cr(II) and compounds having at least one metal ion bonded to at least one organic ligand and the metal ion is selected from one or more of Co(II), Mg(II), Y(III), Cr(III) and a lanthanide series metal ion in the 3+ oxidation state, to convert at least a portion of the organic isocyanate to the one or more urea compounds.

2. The method of claim 1 wherein the metal ion is Co(II) or Mg(II).

3. The method of claim 2 wherein at least one organic ligand is an arene ligand.

4. The method of claim 3 wherein the arene ligand is cyclopentadienyl or methylcyclopentadienyl.

5. The method of claim 1 wherein the organometallic catalyst is one or more of bis(cyclopentadienyl) Co(II), bis(cyclopentadienyl) Mg(II), bis(cyclopentadienyl) Cr(II), tris(cyclopentadienyl) Gd(III), tris(cyclopentadienyl) Y(III), tris(cyclopentadienyl) La(III), bis(methylcyclopentadienyl) Co (II), bis(methylcyclopentadienyl) Mg(II), bis(methylcyclopentadienyl) Cr(II), tris (methylcyclopentadienyl) Gd(III), tris(methylcyclopentadienyl) Y(III), tris(methylcyclopentadienyl) La(III), a tris(cyclopentadienyl) lanthanide series metal and a tris(methylcyclopentadienyl) lanthanide series metal.

6. The method of claim 2 wherein at least one organic ligand is a β-diketone.

7. The method of claim 6 wherein the organometallic catalyst is one or more of Co(II) acetylacetonate and bis(2, 4-pentanedionato) Mg(II).

8. The method of claim 1 wherein the organic isocyanate includes unsubstituted phenyl isocyanate.

9. The method of claim 1 further comprising a step of producing a process stream in an isocyanate manufacturing process by separating a process solvent from a polyisocyanate product produced in a step of reacting a polyamine with phosgene in solution in the process solvent, and the solution of the organic isocyanate in a liquid nonpolar organic solvent is or includes the process stream.

10. The method of claim 9 wherein the polyamine is MDA and/or PMDA.

11. The method of claim 10 further comprising a step of recycling at least a portion of the one or more urea compounds into the isocyanate manufacturing process and reacting the recycled one or more urea compounds with a polyisocyanate to form one or more biuret compounds.

12. The method of claim 11 further comprising reacting the recycled one or more urea compounds with a polyisocyanate to form one or more biuret compounds during the step of separating the polyisocyanate produce from the process solvent.

13. The method of claim 1 further comprising the step of separating at least a portion of the one or more nonpolar organic solvents from the one or more urea compounds.

14. An MDI and/or polymeric MDI manufacturing process, comprising the steps of:
   a) reacting aniline with formaldehyde to produce a mixture of methylene dianiline (MDA), one or more polymethylene polyanilines having at least three aniline groups (PMDA) and unreacted aniline in a solvent;
   b) distilling aniline from the mixture produced in step a) to produce a process stream containing the MDA, PMDA and residual aniline;
   c) phosgenating the process stream from step b) in a non-polar solvent to form an isocyanate process stream containing the non-polar solvent, MDI, one or more polymethylene polyphenylisocyanates that have at least three phenyl isocyanate groups (PMDI) and phenyl isocyanate;

d) separating MDI and PMDI from the isocyanate process stream obtained in step c) by distillation to produce a solvent stream containing the non-polar solvent, 0.2 to 10 weight percent phenyl isocyanate based on the weight of the solvent stream and up to 5 weight percent, based on the weight of the solvent stream, of MDI and/or PMDI;

e) reacting the solvent stream obtained in step d) in the presence of at least 0.025 wt.-% of an organometallic catalyst, based on the weight of the phenyl isocyanate, wherein the organometallic catalyst is selected from the group consisting of bis(cyclopentadienyl) Cr(II), bis (methylcyclopentadienyl) Cr(II) and compounds having at least one metal ion bonded to at least one organic ligand and the metal ion is selected from one or more of Co(II), Mg(II), Y(III), Cr(III) and a lanthanide series metal ion in the 3+ oxidation state, to convert at least a portion of the phenyl isocyanate to 1,3-diphenylurea and optionally aniline, and optionally to thermally deactivate the organometallic catalyst; and f) recycling 1,3-diphenylurea and optionally non-polar solvent and optionally residues from the thermal deactivation of the catalyst, from step e) directly or indirectly into step d), whereby at least a portion of the 1,3-diphenylurea reacts with at least a portion of the MDI and/or PMDI to form biuret compounds.

* * * * *